United States Patent

Bleuse et al.

[11] Patent Number: 5,854,676
[45] Date of Patent: Dec. 29, 1998

[54] METHOD AND DEVICE FOR CONTINUOUS ANALYSIS OF THE COMPOSITION OF A GASEOUS ATMOSPHERE CONTAINING PARTICLES OF MATERIAL IN SUSPENSION

[75] Inventors: Patrick Bleuse, Bois D'Avray; Pierre Clausin, Ville D'Avray; Gilles Guéné, Elancourt; Eric Wurmser, Saint Cyr L'Ecole, all of France

[73] Assignee: Proengin S.A., France

[21] Appl. No.: 900,455

[22] Filed: Jul. 25, 1997

[30] Foreign Application Priority Data

Jul. 25, 1996 [FR] France ................................... 96 09498

[51] Int. Cl.$^6$ .................................................. G01N 21/72
[52] U.S. Cl. ............................................. 356/315; 356/417
[58] Field of Search ...................................... 356/315, 417, 356/335

[56] References Cited

U.S. PATENT DOCUMENTS 2,730,005  1/1956  Vonnegut .
3,644,743  2/1972  Binek et al. ............................ 356/417

FOREIGN PATENT DOCUMENTS 15982898  12/1970  Germany .
716163  9/1954  United Kingdom .

Primary Examiner—F. L. Evans
Attorney, Agent, or Firm—William A. Drucker

[57] ABSTRACT

A device for continuous analysis of the composition of a gaseous atmosphere containing particles of material in suspension includes a burner equipped with a prism; an intensifier which produces an intensified image of the spectrum produced by the dispersive component on photodiodes; a register which stores data detected by the photodiodes; a microcomputer which periodically reads the register and compares the data read with reference data to identify the elements looked for; and a counter which counts the number of times that the same component is identified per unit time in order to determine the number of particles per unit volume. The device can be implemented in the form of a portable, self-contained apparatus.

12 Claims, 1 Drawing Sheet

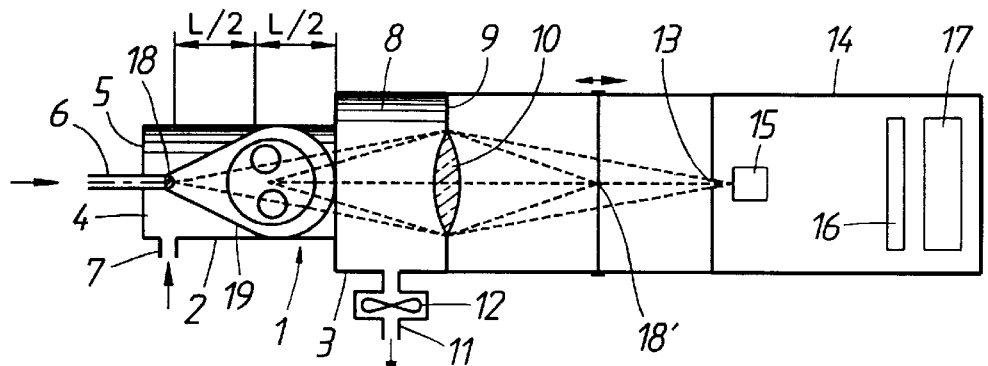
FIG. 1
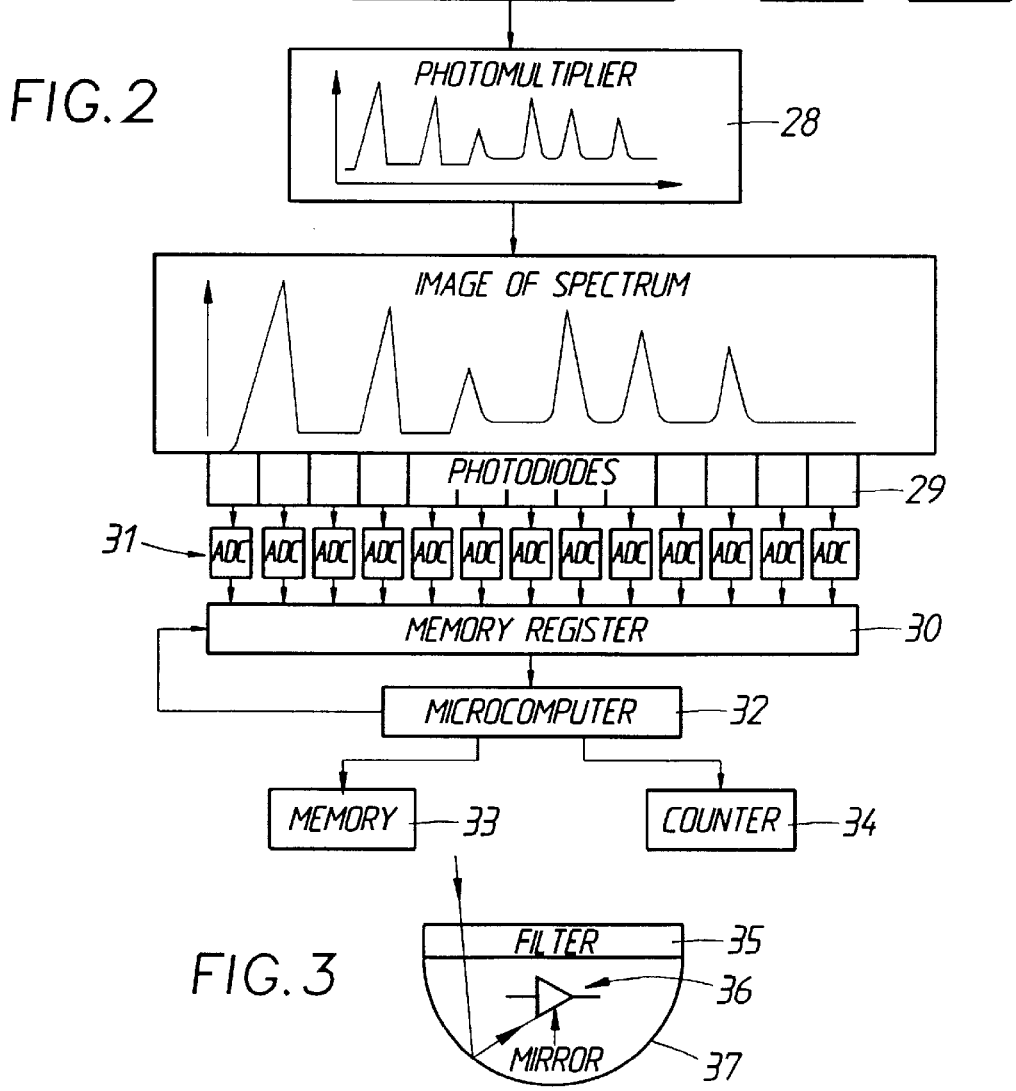
FIG. 2
FIG. 3

METHOD AND DEVICE FOR CONTINUOUS ANALYSIS OF THE COMPOSITION OF A GASEOUS ATMOSPHERE CONTAINING PARTICLES OF MATERIAL IN SUSPENSION

BACKGROUND OF THE INVENTION

1. Field of the Invention

The present invention concerns a method and a device for continuous qualitative and quantitative analysis of the composition of a gaseous atmosphere containing particles of material in suspension. It applies in particular, but not exclusively, to the detection of biological substances such as e.g. bacteria present in the ambiant air.

2. Description of the Prior Art

The methods usually employed for analyzing particles in suspension in air generally consist in concentrating the particles, for example in a filter, and then analyzing the material retained by the filter.

This is a discontinuous type analysis method requiring a device for sampling the air by filtration and a laboratory for analyzing the filtrates.

A method of this kind can therefore not carry out continuous analysis in situ providing results instantaneously.

A particular aim of the invention is therefore to achieve this result using a portable self-contained apparatus that is of low cost given the nature of the results that it can provide, and requiring no previous treatment of the gaseous atmosphere to be analyzed.

The invention is based on the observation that upon spectrophotometric analysis of light emitted by a flame resulting from the combustion of a flow of air laden with particles in hydrogen, each particle produces a flash the luminous emissions from which can be broken down to generate a spectrum representative of the composition of the particle that produced the flash.

In contrast to spectrophotometric analysis of an absorption spectrum, in an analysis of an emission spectrum (atomic spectrometry):

the number of products identifiable is limited to the finite number of products which react optically in the flame, the number of reference spectra needed to identify products looked for is also limited, the problem of interference is much less acute.

The invention therefore proposes to exploit all these features to provide a method that can be used by a portable self-contained spectrophotometric device that is relatively simple and of low cost.

SUMMARY OF THE INVENTION

To this end, the method of the invention comprises the following operations:

continuously combusting a gaseous atmosphere (e.g. a flow of ambiant air) to be analyzed in a flow of combustion-supporting gas (e.g. hydrogen) at a constant flowrate, decomposing the luminous radiation to obtain instantaneously a luminous spectrum, periodically sampling all of the spectrum and converting the samples into digital data representative of the spectrum, comparing this digital data with digital data representative of previously memorized reference spectra, identifying a substance looked for if the comparison reveals similarity between the digital data resulting from the above-mentioned conversion and the digital data representative of a reference spectrum, and counting the number of times a same component or a same set of components has been identified during a predetermined time period in order to determine the composition of the particles in suspension in the atmosphere and their number per unit volume.

Advantageously, said method could comprise in particular:

detection of the flashes produced by the combustion of particles present in the gaseous atmosphere to be analyzed the intensity of which exceeds a given threshold, as well as detection of the luminous emissions between flashes, a first spectrometric analysis of the luminous radiation between the flashes so as to know the composition of the gas carrying the particles, a second spectrometric analysis of the luminous radiation during the flash so as to know the composition and/or to identify the particles contained in the gas.

Said second spectrometric analysis could comprise digital processing in order to subtract from the spectral values obtained during the flashes, the spectral values obtained between flashes, and to compare the resulting values with previously-memorized values so as to identify the particles which produced the flash when the comparison reveals a similitude, then to count them selectively.

Moreover, the size of the particles could be identified on the basis of the detection of the luminous intensity of the flash.

It has been found that this solution is particularly efficient for detecting and counting the particles of biological substances (e.g. bacteria) identification of which is obtained from the ratio of the constituents detected during the flash, said ratio being compared with previous-memorized reference ratios.

The decomposition of the luminous emissions can be effected in a spectrophotometer using:

fixed interference filters associated with detectors, a static interference filter the filtration power of which varies continuously as a function of wavelength, this filter being associated with a strip of detectors (photodiodes), or a dispersive optic (prism or grating) for breaking the light down into a luminous spectrum detectable by a fixed opto-electronic detection system, an interferometer associated with a processing circuit effecting a Fourier transform.

The burner in which the mixture of air and hydrogen is combusted can advantageously comprise a focusing optic of the type described in French patent application 96 00703 filed in the name of then present applicant in order to improve the signal/noise ratio to allow the use of photo-intensifiers such as photomultipliers, for example.

One embodiment of the invention is described hereinafter by way of non-limiting example and with reference to the accompanying drawings.

BRIEF DESCRIPTION OF THE DRAWINGS

FIG. 1 is a schematic representation of a flame spectrophotometer of the invention.

FIG. 2 is a block schematic showing an emission spectrum and the opto-electronic detection system for digitizing it.

FIG. 3 is a schematic representation of an opto-electronic detection cell associated with an interference filter.

DETAILED DESCRIPTION OF THE PREFERRED EMBODIMENT

In the example shown in FIG. 1 the flame spectrophotometer uses a tubular burner 1 comprising two coaxial nozzles 2, 3 with different diameters axially offset relative to each other. The two nozzles 2, 3 delimit two successive chambers, namely:

- a combustion chamber 4 open at one end and closed at the other end by an end wall 5 through which passes a coaxial inlet conduit 6 for the gas to be analyzed. This chamber 4 is also connected to a hydrogen injection conduit 7 which passes radially through the longitudinal wall of the nozzle 2,
- a stabilization chamber 8 into which the combustion chamber 4 leads, this chamber 8 being closed at one end by the nozzle 2 and at the other end by a closure member 9 having a coaxial circular opening in which is mounted a lens 10.

The stabilization chamber 8 has a lateral exhaust orifice connected to an exhaust circuit 11 provided with an aspirator turbine 12 driven by a motor.

The lens 10 is designed to focus the light generated by the inner cone of the flame that propagates in the combustion chamber 4 onto the entry slit 13 of a spectrophotometer 14 which is, for example, of the conventional type using a dispersive component 15 (prism, grating, interference filter) and a detection system 16 that can comprise a strip of intensified photodiodes or a photomultiplier connected to a processor circuit 17.

This spectrophotometer operates in the following manner:

The combination of the chambers 4 and 8 is depressurized by the turbine 12 so as to aspirate gas to be sampled in the inlet conduit 6.

Inside the nozzle 2 the aspirated gas flow mixes with the injected flow of hydrogen so that combustion occurs at the exit of the conduit 6, generating a flame which propagates in the combustion chamber.

This flame comprises an inner cone 18, of small dimensions but relatively bright, which is extended by an outer area 19 extending virtually over the whole length L of the nozzle 2.

To block the luminous radiation generated by the inner cone 18 and therefore the continuum, the lens 10 is adjusted to obtain an image of the inner cone 18 upstream of the slit 13 and an image of the middle part of the outer area 19 at the slit 13 of the spectrophotometer 14.

A mask 18' with the same dimensions is provided to block the propagation of light rays emitted by the inner cone 18 towards the slit.

In the example shown in FIG. 2, the burner and the focusing optic are represented schematically by blocks 25 and 26. The dispersive component (block 27) is schematically represented by a prism which generates a luminous spectrum applied to the input of an intensifier 28 such as a multichannel photomultiplier. The image of the spectrum intensified in this way is applied to a photosensitive surface consisting here of a strip of photodiodes 29.

The output of each of the photodiodes 29 is connected to one cell of a memory register 30 by an analog/digital converter 31 which supplies a digital signal representative of the intensity of the radiation detected by the photodiode 29.

The memory register is controlled by a microcomputer 32 which reads it periodically.

The microcomputer 32 comprises a memory 33 storing data relating to a plurality of reference spectra corresponding to the elements looked for, or even data relating to ratios of sets of constituents allowing definition of biological substances.

It compares the data contained in the register at the time of each reading (intensity spectrum as a function of wavelength) to the reference data and detects identity or similarity, enabling identification of the components of the spectrum produced from the emission of the burner 25 and therefore any of the components looked for that may be present.

The algorithm employed may be a multichannel analysis algorithm of a type known in itself, based on matrix and statistical processing, for example.

Each time it detects a component during emission of a flash it increments a counter 34 so that it is possible to determine a number of particles containing the component per unit time and therefore the concentration of this component in the atmosphere analyzed. Each particle entering the flame produces a flash of limited duration so that by adjusting the reading frequency (sampling frequency) it is possible to establish a relationship between the number of times that the microprocessor identifies a component or even a set of components identifying a particle, and the number of particles of each kind of particles identified entering the flame.

Of course, the invention is not limited to the embodiment previously described.

Accordingly, instead of using a dispersive optic producing the emission spectrum of the flame it would be equally possible to produce an elongate light beam, possibly intensified and projected onto a detector strip, comprising, for example, as shown in FIG. 3:

- a static interference filter 35 the filtering power of which varies as a function of the wavelength (this filter possibly consisting in a multiplicity of juxtaposed filter elements),
- a strip of photodiodes 36 adapted to detect the luminous radiation passing through the filter 35, and
- optionally, a focusing optic such as a curved mirror 37, for example, a spherical or parabolic mirror, for example, for concentrating the filtered luminous radiation onto each of the photodiodes 36.

Likewise, the invention is not limited to analyzing the composition and counting the particles present in the atmosphere. It can also be used to determine the composition of the gaseous atmosphere by spectrophotometry between emission of flashes resulting from the combustion of the particles.

If the concentration of the particles in the atmosphere is too high for the particles to be counted, the atmosphere can be diluted according to a known method. In this case, it must be taken care that the dilution mode does not give rise to a selection of particles. Of course, the dilution can be obtained by adding a further gas flow and/or by varying the gas flow and consumption characteristics.

There is claimed:

1. A method of analyzing the composition of a gaseous atmosphere containing particles in suspension, comprising the following operations:

- continuously combusting a gaseous atmosphere to be analyzed in a flow of combustion-supporting gas at a constant flowrate,
- decomposing the luminous radiation to obtain instantaneously a luminous spectrum,
- periodically sampling all of said spectrum and converting the samples into digital data representative of the spectrum,
- comparing these digital data with digital data representative of previously memorized reference spectra, identifying a substance looked for if the comparison reveals similarity between the digital data resulting from said conversion and the digital data representative of a reference spectrum, counting the number of times a same component or a same set of components has been identified during a predetermined time period in order to determine the composition of the particles in suspension in the atmosphere and their number per unit volume.

2. The method claimed in claim 1, comprising:

detection of the flashes produced by combustion of particles present in the gaseous atmosphere to be analyzed the intensity of which exceeds a given threshold, as well as detection of the luminous emission between flashes, a first spectrometric analysis of the luminous radiation between flashes so as to know the composition of the gas carrying the particles, and a second spectrometric analysis of the luminous radiation during the flash so as to know the composition and/or identify the particles contained in the gas.

3. The method claimed in claim 2, comprising digital processing in order to subtract from the spectral values obtained during the flashes the spectral values obtained between flashes and to compare the resulting values with previous-memorized values so as to indentify the particles having produced the flash when the comparison reveals a similitude, then to count them selectively.

4. The method as claimed in claim 2, comprising the determination of the size of the particles based on the detection of the luminous intensity of the flashes.

5. The method as claimed in claim 2 for detecting and counting particles of biological substances, wherein identification of the particles is obtained by comparing the ratio between the constituents detected during the flashes with previously-memorized reference ratios.

6. The method claimed in claim 1 wherein said atmosphere is the ambient air and said combustion-supporting gas is hydrogen.

7. The method claimed in claim 1 wherein said decomposition of said luminous emissions is effected in a spectrophotometer using interference filters in front of opto-electronic detectors onto which the luminous radiation is focused.

8. The method claimed in claim 1 wherein said decomposition of said luminous emissions is effected in a spectrophotometer using a static interference filter the filtering power of which varies as a function of wavelength, said filter being associated with a strip of detectors.

9. The method claimed in claim 1 wherein said in decomposition of said luminous emissions is effected in a spectrophotometer using a dispersive optic to decompose the light into a luminous spectrum detectable by a fixed opto-electronic detection system.

10. The method claimed in claim 1 wherein said decomposition of said luminous emissions is effected in a spectrophotometer using an interferometer associated with a processor circuit effecting a Fourier transform.

11. The method claimed in claim 1 wherein the spectrum of the radiation produced by said combustion is photo-intensified.

12. A device for implementing the method as claimed in claim 1 comprising a burner equipped with a focusing optic, a component for dispersing the focused luminous radiation which generates a luminous spectrum applied to the input of an intensifier which produces an intensified image of the spectrum on opto-electronic photosensitive means, a memory register storing data detected by said photosensitive means and a microcomputer or electronic means that reads said register periodically and compares the data read in this way with data relating to a plurality of reference spectra corresponding to the elements looked for, said microcomputer incrementing a counter each time it detects and identifies a component by virtue of said comparison during the emission of a flash.

* * * * *